Dec. 15, 1964 W. E. SILVA Plant Pat. 2,464
APPLE TREE
Filed Oct. 7, 1963
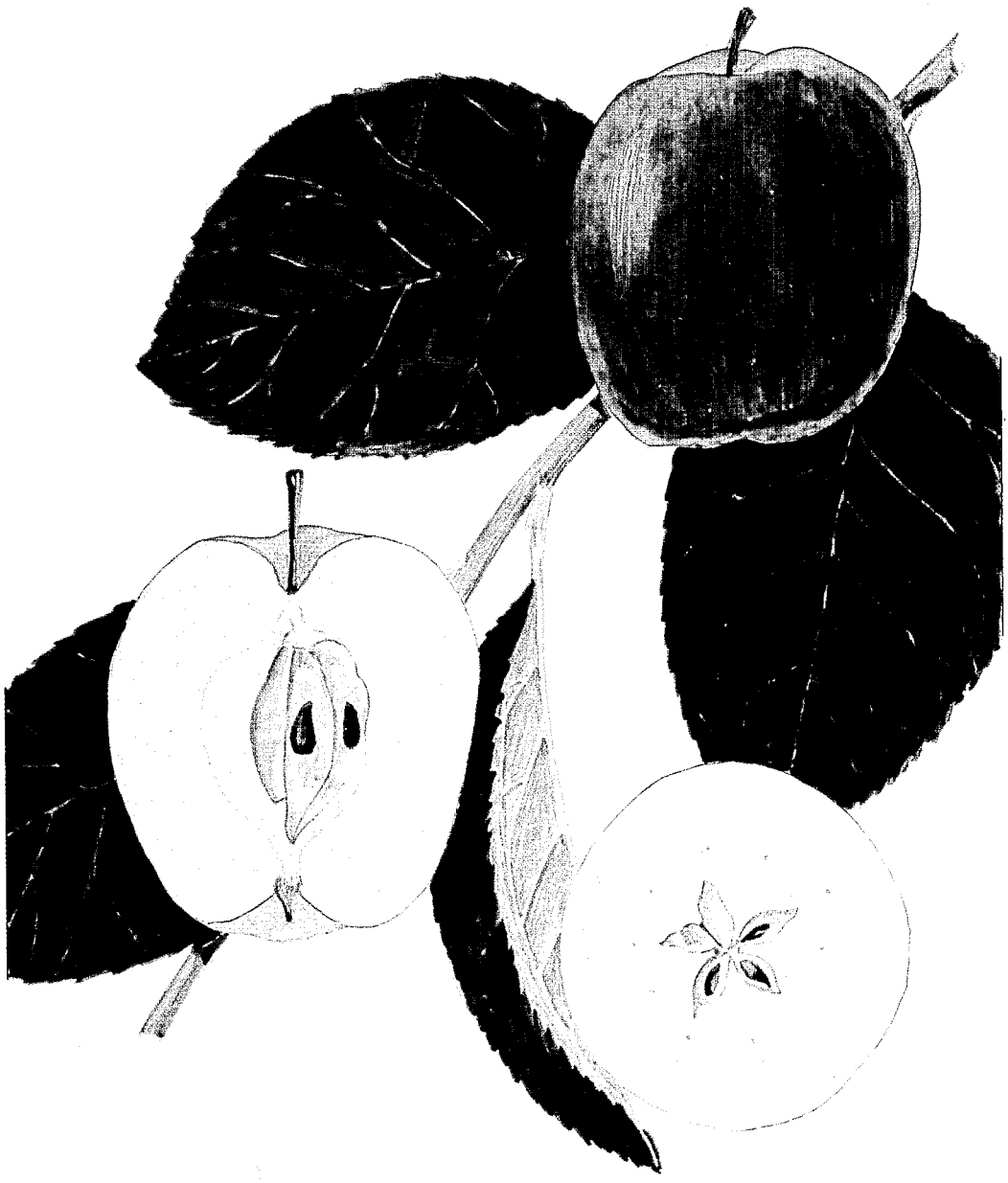
WITNESS
Samuel H. Troy
INVENTOR
WILLIAM E. SILVA
by Rummler & Snow
ATTYS.

United States Patent Office

Plant Pat. 2,464
Patented Dec. 15, 1964

2,464
APPLE TREE

William E. Silva, 408 Water Trough Road,
Sebastopol, Calif.

Filed Oct. 7, 1963, Ser. No. 314,573
1 Claim. (Cl. Plt.—34)

This disclosure concerns a new and distinct variety of apple tree which was developed by me through extensive breeding efforts, since 1948, at my breeding grounds at Sebastopol, California. My objective was to produce an early solid-red apple which would be firm and have superior keeping qualities, for marketing from early fall until winter without the need for cold storage, and which would have a good test rating for solids and sugar content.

My new variety of apple tree, which originated as a seedling of Baldwin × Red Bellflower (both unpatented) with Baldwin as the pollen parent, has amply accomplished these objectives and asexual reproduction of the new variety, by budding and by grafting, at my trial grounds at Sebastopol, California, has demonstrated that its novel and distinctive characteristics, hereinafter set forth, are fixed and hold true. The present method of propagation is by budding and a sufficient stock has been created so that commercial exploitation of my new variety can now be begun.

The accompanying drawing, in full color, shows typical specimens of the fruit and foliage of my new variety of apple tree, one of the specimens of fruit being shown in elevation and others being shown in axial cross-section and in transverse cross-section.

The following is a detailed description of my new variety of apple tree, the color designations being according to "A Dictionary of Color" by Maerz and Paul.

*The Tree*

Origin: Seedling.
- *Seed parent.*—Red Bellflower (unpatented).
- *Pollen parent.*—Baldwin.

Classification: Hybrid Malus.

Growth habit: Vigorous and upright. Heavy producer of fruit on many spurs, each spur bearing one and often two apples.

Trunk: Stocky and smooth.

Branches: Upright attachment, with 3 to 4 inch long spurs occurring at 5 to 6 inch intervals. Color—Plate 16, L–10.

Leaves: Abundant, medium size, averaging approximately 2½ inches wide and 4 inches long; oval shaped with serrate margins.
- *Color.*—Top side—Plate 22, L–8. Under side—Plate 21, J–5. Ribs—Plate 19, J–1.
- *Pubescence.*—Very fine, uniformly distributed, on underside of leaf.
- *Petiole.*—Generally cylindrical ¾ to 1 inch long.
- *Stipules.*—Free, foliaceous, oblanceolate appendages, ⅜ to ½ inch long.

Flowers: Medium size—approximately 1 inch in diameter with five white petals having light pink margins. First bloom, about 10th of May. Full bloom by 20th of May (in northern California).
- *Stamens.*—Very short, relative to those in blooms of parent varieties, light green in color and anthers have light yellow pollen.
- *Filaments.*—Light green in color, 1/12 inch long.
- *Pistils.*—Syncarpous with 5 stigmas, light green in color.

Disease resistance: No indication of mildew or other apple tree diseases and pests, as observed in normal orchard growth at Sebastopol, California.

*The Fruit*

Shape: Oblong-ovoid. Generally symmetrical.

Size: 3½ inches long, axially; transverse diameter 2⅝ to 3 inches.

Color: Ripe red, Plate 4, L–4 to L–6 with yellow undercoat, Plate 9, L–3. Distribution—substantially uniform over-all, except for light area due to effect of shade.

Stem: Approximately 1 inch long and 3/16 inch diameter. Color, Plate 8, L–7 undercoat with gray overtone, Plate 14, E–5. Cavity—⅝ inch wide, ¾ inch deep.

Calyx: Color, Plate 13, L–1 to L–2. Basin—⅝ inch wide, 5/16 inch deep. No pubescence, cleans and drops all petalage.

Seed: Color, Plate 14, A–12. Size and number—5/16 inch long. 3 to 5 in number—generally 5 seeds.

Skin: Thin, smooth and not tough. No scarf skin and no wax.

Flesh: Juicy and with firm texture.
- *Color.*—Generally whitish yellow, Plate 10, B–1 to Plate 10, E–1 adjacent core. Greenish colortone in core—Plate 17, K–1 to K–4.
- *Aroma.*—Prominent and pleasant.
- *Flavor.*—Sweet.
- Soluble solids 16.4%, as tested by Horticultural Commision at Santa Rosa, Calif.

Maturity season: Friut begins to ripen during the last 10 days of July and is ripe, ready for picking for market by mid-August.

Keeping quality: Extraordinarily good, fruit keeping well and maintaining good quality without cold storage in cool, ventilated, rock-built cellar at least until mid-December. Under cold storage test the fruit remained firm and of high quality with no discernible signs of deterioration or shrinkage after more than 6 months of 40° F. refrigeration.

Use: Excellent apple for early fall trade. Very good for eating out of hand, for pies, canning and sauce.

In general, my new variety of solid-red apple is particularly distinguished by its early ripening season and the fact that it is the first of the red applies to ripen in the northern California area where many other varieties of red apples are also grown; its relatively high percentage of solids and sugar content for an apple ripening so early; its very extraordinary keeping quality, without cold storage as well as under refrigeration, which provides excellent commercial advantages; and its relatively high productivity of fruit of substantially uniform size and quality.

Having thus described my new variety of apple tree, I claim:

A new and distinct variety of apple tree, substantially as shown and described, particularly characterized as to novelty by the deep red color of its very early ripening fruit which comes to marketing maturity in mid-August; by the relatively high percentage of soluble solids and sweet flavor for a fruit maturing so early in the season; and by the excellent and extraordinary keeping quality of the ripened fruit without cold storage.

No references cited.

ABRAHAM G. STONE, *Primary Examiner.*